(12) United States Patent
Maleki et al.

(10) Patent No.: US 11,976,737 B2
(45) Date of Patent: *May 7, 2024

(54) CHECK VALVE WITH SECONDARY BACKFLOW SEAL

(71) Applicant: CareFusion 303, Inc., San Diego, CA (US)

(72) Inventors: Shervin Maleki, Long Beach, CA (US); Eugene Mason, La Habra Heights, CA (US); Raymond P. Feith, Chino Hills, CA (US)

(73) Assignee: CareFusion 303, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/670,321

(22) Filed: Feb. 11, 2022

(65) Prior Publication Data

US 2022/0163135 A1 May 26, 2022

Related U.S. Application Data

(63) Continuation of application No. 16/842,664, filed on Apr. 7, 2020, now Pat. No. 11,248,719.

(51) Int. Cl.
*F16K 15/14* (2006.01)

(52) U.S. Cl.
CPC .......... *F16K 15/148* (2013.01); *F16K 15/142* (2013.01); *Y10T 137/7867* (2015.04); *Y10T 137/7868* (2015.04)

(58) Field of Classification Search
CPC ...... F16K 15/14; F16K 15/142; F16K 15/148; A61M 2039/2406; A61M 2039/2446; A61M 2039/2453; A61M 2039/2466
See application file for complete search history.

(56) References Cited

U.S. PATENT DOCUMENTS

| | | |
|---|---|---|
| 2,163,472 A | 6/1939 | Shimer |
| 2,495,880 A | 1/1950 | Volpin |
| 4,373,550 A | 2/1983 | Yelich |
| | (Continued) | |

FOREIGN PATENT DOCUMENTS

WO    WO-2010107597 A1    9/2010

OTHER PUBLICATIONS

International Search Report and Written Opinion for Application No. PCT/US2021/026046, dated Jul. 19, 2021, 12 pages.

(Continued)

*Primary Examiner* — Kevin F Murphy
(74) *Attorney, Agent, or Firm* — Morgan, Lewis & Bockius LLP

(57) ABSTRACT

Check valve are disclosed having a primary seal and a secondary seal, where the primary and secondary seals resist movement of a fluid through the check valve, and the secondary seal can provide a backup seal in an instance where the check valve does not function as intended. The primary and secondary seals can be formed by first and second sealing ridges, respectively, and a valve body can be positioned within the check valve, between a valve support, the first sealing ridge, and a second sealing ridge. The valve body is configured to move relative to the first and second sealing ridges, and can have a position wherein a portion of the valve body is engaged against any of the first and second sealing ridges.

20 Claims, 8 Drawing Sheets

(56) References Cited

U.S. PATENT DOCUMENTS

| | | | |
|---|---|---|---|
| 4,532,958 | A | 8/1985 | Napolitano |
| 4,615,693 | A * | 10/1986 | Paradis ................. F16K 15/148 604/323 |
| 4,762,149 | A * | 8/1988 | Pickl, Jr. ............... F16K 15/141 137/854 |
| 5,052,435 | A | 10/1991 | Crudup |
| 6,651,693 | B2 | 11/2003 | Simmons |
| 8,186,377 | B2 | 5/2012 | Ishitoya |
| 8,607,825 | B2 | 12/2013 | Gerlich |
| 11,248,719 | B2 * | 2/2022 | Maleki .................... F16K 35/04 |
| 2008/0058720 | A1 | 3/2008 | Spohn et al. |
| 2019/0316695 | A1 | 10/2019 | Feith et al. |

OTHER PUBLICATIONS

Written Opinion of the International Preliminary Examining Authority for Application No. PCT/US2021/026046, dated Mar. 11, 2022, 9 pages.

International Preliminary Report on Patentability from the International Preliminary Examining Authority for Application No. PCT/US2021/026046, dated Jul. 18, 2022, 21 pages.

* cited by examiner

CHECK VALVE WITH SECONDARY BACKFLOW SEAL

CROSS REFERENCE TO RELATED APPLICATIONS

This application is a continuation application of U.S. application Ser. No. 16/842,664, filed on Apr. 7, 2020, the disclosure of which is incorporated herein by reference in its entirety.

BACKGROUND

The present disclosure relates generally to controlling the direction of a fluid flow. More specifically, the present descriptions relate to control of fluid flow using check valve.

Check valves are devices that permit a fluid to move through a valve in a first direction and restrict or resist movement of a fluid through the valve in a second direction that is different than the first direction. The movement of a fluid through the valve in the second direction is commonly referred to as backflow.

Check valves can be used in many types of application, including, pumps, such as piston-driven and diaphragm pumps; fluid systems for industrial processes, including chemical and power plants; fluid control systems, such as irrigation sprinklers and drip irrigation; and in medical applications, such as valves for the heart ventricles, infusion therapy, and movement of other fluids and/or medicaments.

A check valve can include a valve body that is generally shaped as a disk forming a diaphragm. The valve body can move to permit or resist movement of fluid through a passageway of the check valve. In some instances, the valve body can have a closed position in which the valve is engaged against a portion of the check valve to resist movement of a fluid therethrough, and the valve body can have an open position in which the valve moves relative to the portion of the check valve to permit movement of a fluid therethrough.

A check valve can move to an open position to permit fluid therethrough by a fluid pressure or engagement of a fluid against the valve. The check valve moves from the closed position to the open position when a cracking pressure of the check valve is achieved. The cracking pressure corresponds to a difference between the pressure in the fluid passageway upstream of the valve body, relative to the pressure in the fluid passageway downstream of the valve body. In some check valves, the valve body moves to an open position when a positive pressure differential is applied to the valve body, for example, when a pressure upstream of the valve body is greater than a pressure downstream of the valve body.

A valve body can move to the closed position when the positive pressure differential is decreased, removed, or reversed. For example, the valve body can move to the closed position when a fluid backflow occurs, i.e., when a fluid moves from the downstream portion of the check valve toward the upstream portion of the check valve. A negative pressure differential, such as when the fluid pressure downstream of the valve body is greater than the fluid pressure upstream of the valve body, can cause the valve body to move to the closed position. In some instances, the inherent resilience of the valve body can also enable the valve body to move to the closed position.

SUMMARY

A check valve can fail to function as intended when the valve body does not move to the closed position or does not resist a backflow of fluid through the check valve. For example, a check valve can fail to move to the closed position or resist a backflow of fluid when a particulate or debris becomes lodged in the check valve. In some instances, a particulate or debris can become embedded between the valve body and another portion of the check valve such that the valve body does not completely resist fluid flow or obstruct the fluid passage.

A check valve can also fail to function as intended when a pressure differential between the upstream and downstream portions of the fluid passageway cause the valve to become unseated or move in an unintended manner. For example, when the downstream pressure is significantly greater than an intended operating parameter of the check valve, the valve body can become dislodged from a valve seat or support surface, and the valve body can move toward or become extruded into the upstream portion of the fluid passageway.

In accordance with at least some embodiments disclosed herein is the realization that although check valves can be designed with specific performance characteristics, certain problems can occur during use, manufacturing, and assembly of the check valve. For example, particulate or debris in a fluid can become lodged in the check valve, thereby preventing the valve from closing as intended.

An aspect of the present disclosure provides a check valve having a housing comprising an inner cavity, a first port, and a second port, wherein an upstream fluid passageway extends through the first port to the inner cavity, and a downstream fluid passageway extends through the second port to the inner cavity; a first sealing ridge, extending into the inner cavity, and comprising a perimeter that extends around the first port; a second sealing ridge, extending into the inner cavity, and comprising a perimeter that extends around the upstream fluid passageway such that the first seal ridge is between the first port and the second seal ridge; a valve support comprising a valve support surface; and a valve body positioned within the inner cavity, the valve body comprising a first portion that is moveable relative to the first sealing ridge, a second portion that is moveable relative to the second sealing ridge, and third portion engaged against the valve support surface.

Some instances of the present disclosure provide a check valve comprising a housing having an inner cavity, a first port, and a second port, wherein an upstream fluid passageway extends through the first port to the inner cavity, and a downstream fluid passageway extends through the second port to the inner cavity; a first sealing ridge, extending into the inner cavity, and comprising a perimeter that extends around the first port; a second sealing ridge, extending into the inner cavity, and comprising a perimeter that extends around the upstream fluid passageway such that the first seal ridge is between the first port and the second seal ridge; and a valve body positioned within the inner cavity and comprising a first closed position, wherein a first portion of the valve body is engaged against the first sealing ridge, and a second portion of the valve body is spaced apart from the second sealing ridge, an open position, wherein the first and second portions of the valve body are spaced apart from the first and second sealing ridges, respectively, and a second closed position, wherein at least a portion of the first portion of the valve body is engaged against the first sealing ridge and a second portion of the valve body is engaged against the second sealing ridge.

Some instances of the present disclosure provide a method of controlling flow comprising providing a check valve defining an inner cavity with a fluid passageway extending therethrough, a first sealing ridge, and a second sealing ridge; and providing a valve body within the inner cavity in a first closed position such that a first portion of the valve body is engaged against the first sealing ridge to resist movement of a fluid between upstream and downstream portions of the fluid passageway, and a second portion of valve body is spaced apart from the second sealing ridge; wherein the valve body is moveable to a second closed position such that at least a portion of the first portion of the valve body is engaged against the first sealing ridge and a second portion of the valve body moves toward and engages the second sealing ridge.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

Figure 1:
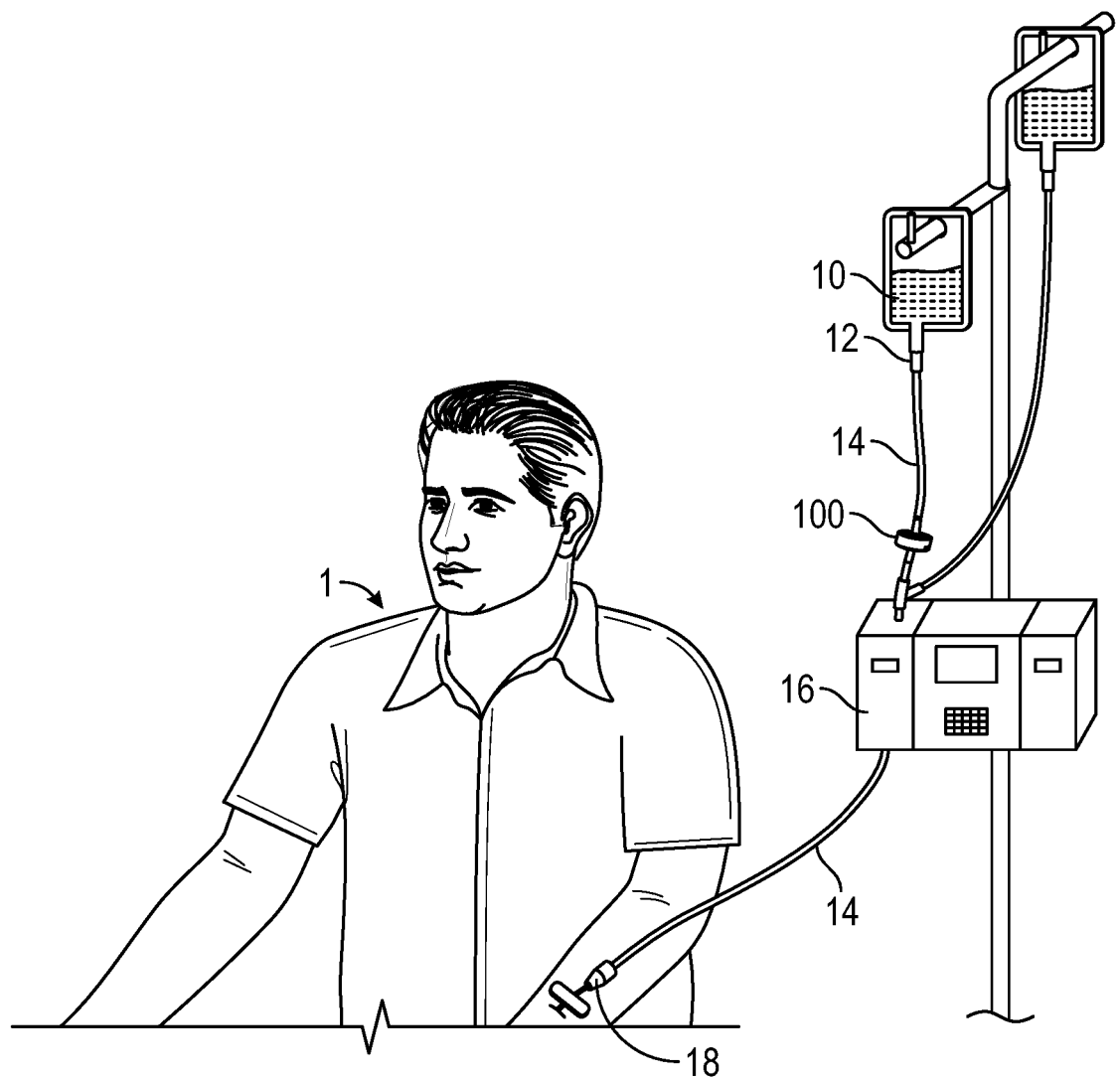
FIG. 1 illustrates a check valve coupled to a patient through intravenous tubing, in accordance with aspects of the present disclosure.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, various applications of such embodiments and modifications thereto, which may occur to those who are skilled in the art, are also encompassed by the general concepts described herein.

In accordance with some embodiments, the present application discloses various features and advantages of a check valve. The check valve can permit a fluid to move through the check valve in a first direction, and resist movement of a fluid through the check valve in a second direction that is different than the first direction, e.g., during backflow through the check valve. The present disclosure also provides features of a check valve that can resist movement of a fluid through the check valve when the valve body does not close as intended. Check valves having features of the present disclosure can resist movement of a fluid through the check valve when the valve body does not close as intended during backflow by including a primary seal and a secondary seal. Additionally, in accordance with some embodiments, the various features and advantages of the present application can increase the reliability of a check valve, simplify manufacturing of the check valve components, and increase the efficiency of assembling the check valve.

In at least some embodiments, the check valve includes a valve body that can have one or more open positions and one or more closed positions. For example, the valve body can have an open position wherein at least a portion of the valve body is moved to permit a fluid to move through a fluid passageway of the check valve. The valve body can have a closed position (e.g., a first closed position) wherein at least a portion of the valve body obstructs or resists movement of a fluid through the fluid passageway, such as during backflow through the check valve. Additionally, the check valve can have another closed position (e.g., a second closed position) wherein another portion of the valve body is moved to obstruct or resist the movement of a fluid through the fluid passageway, such as when the valve body does not obstruct the fluid passageway as intended during backflow through the check valve.

In some embodiments, the valve body includes a first closed position and a second closed position. When the valve body is in the first closed position, a first portion of the valve body obstructs the fluid passageway through the check valve, and when the valve body is in the second closed position, the first portion of the valve body and a second portion of the valve body obstruct the fluid passageway.

The check valve can be configured such that the first portion of the valve body can engage against a first sealing surface of the check valve to form the primary seal, thereby obstructing the fluid passageway, and the second portion of the valve body can engage against a second sealing surface of the check valve to form the secondary seal, thereby also obstructing the fluid passageway. In some aspects of the present disclosure, the primary and secondary seals are positioned in series along the fluid passageway through the check valve. It is contemplated that, in some embodiments, any of the first and second portions of the valve body can move relative to each other and/or another portion of the check valve.

The check valve can include an inlet port and an outlet port, with a fluid passageway extending between the inlet and outlet ports, and a valve body positioned in the fluid passageway and between the inlet and outlet ports. The portion of the fluid passageway, between the inlet port and the valve body forms an upstream portion of the fluid passageway, and the portion of the fluid passageway between the valve body and the outlet port forms a downstream portion of the fluid passageway.

The check valve can have an orientation with the valve body in the first closed position, thereby forming the primary seal. The valve body can be in the first closed position when there is no fluid moving through the fluid passageway or when a cracking pressure of the check valve is not exceeded, such as when a pressure in the upstream portion of the fluid passageway is less than or equal to a pressure in the downstream portion of the fluid passageway. The valve body can also be in the first closed position when a pressure in the downstream portion of the fluid passageway is greater than or equal to a pressure in the upstream portion of the fluid passageway.

In some instances, a particulate or debris can become lodged in the check valve, such as between the valve body and the first sealing surface, thereby preventing the primary seal from forming completely and resulting in a leak between the upstream and downstream portions of the fluid passageway. It is contemplated that other instances may occur in which the primary seal is not formed as intended, such as deformation or damage to the valve body, the sealing surface, or another portion of the check valve.

The valve body can move to the second closed position, thereby forming the secondary seal, when the primary seal is not formed as intended or when a differential pressure between the upstream and downstream portions of the fluid passageway exceeds a threshold value. In some embodiments of the present disclosure, the primary and secondary seals can be formed simultaneously.

In some embodiments, the first and second sealing surfaces are positioned along the upstream portion of the fluid passageway. The second sealing surface is positioned between and the inlet port and the valve body, and the first sealing surface is positioned between the inlet port and the second sealing surface.

The valve body is positioned along the fluid passageway with the first portion of the valve body adjacent to the first sealing surface, and with the second portion of the valve body adjacent to the second sealing surface. The first sealing surface is different than the second sealing surface, and the first portion of the valve body is different than the second portion of the valve body. Any of the first and second sealing surface can be engaged against by the valve body to resist the movement of a fluid along the fluid passageway through the check valve.

Referring now to the figures, FIG. 1 illustrates an example of a check valve 100 in use in accordance with aspects of the present disclosure. The check valve 100 is fluidly coupled with tubing of an intravenous (IV) set being used to deliver a fluid to a patient 1. The IV set includes a medicament bag 10, a drip chamber 12, tubing 14, a pump 16, and an IV catheter 18. In some embodiments, the check valve 100 can be fluidly coupled to the tubing 14 along a portion between the medicament bag 10 and the pump 16, or between the pump 16 and the IV catheter 18. It should be understood that the check valve of the present disclosure can be used in other applications other than IV therapy.

Figure 2:
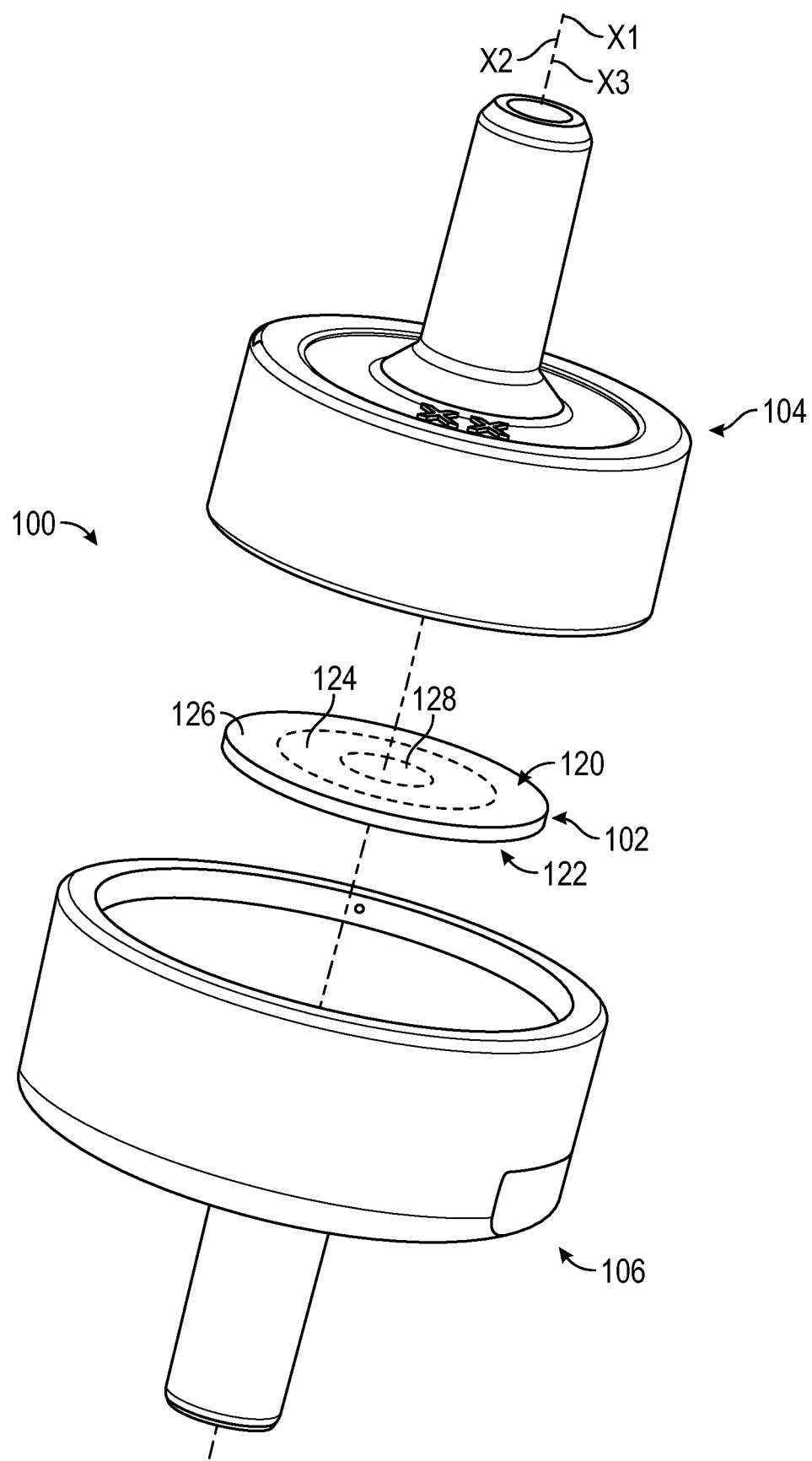
FIG. 2 illustrates an exploded perspective view of the check valve, in accordance with aspects of the present disclosure.

FIG. 2 is a perspective view of an exploded check valve 100 in accordance with some embodiments of the present disclosure. The check valve 100 includes a valve body 102, an upper housing 104, and a lower housing 106. The check valve 100 is configured for the valve body 102 to be positioned between the upper and lower housing 104, 106. In some embodiments, the upper housing 104 forms at least a portion of an upstream fluid passageway and the lower housing 106 forms at least a portion of a downstream fluid passageway.

A radial center of the valve body 102, the upper housing 104, and the lower housing 106 define an axis X1 through the check valve 100.

The valve body 102 includes a top surface 120 and a bottom surface 122. The valve can also include segments or portions, such as a first portion 124 proximal the center of the valve body 102 (e.g., axis X1), and a second portion 126 that can be located radially outward relative to the first portion 124. In some embodiments, the valve body includes a third portion 128 that can be located radially inward relative to the first portion 124, such that the first portion of the valve is positioned between the second and third portions 126, 128. In some aspects of the present disclosure, any of the first, second, and third portions 124, 126, 128 can be located along the bottom surface 122 of the valve body.

Figure 3:
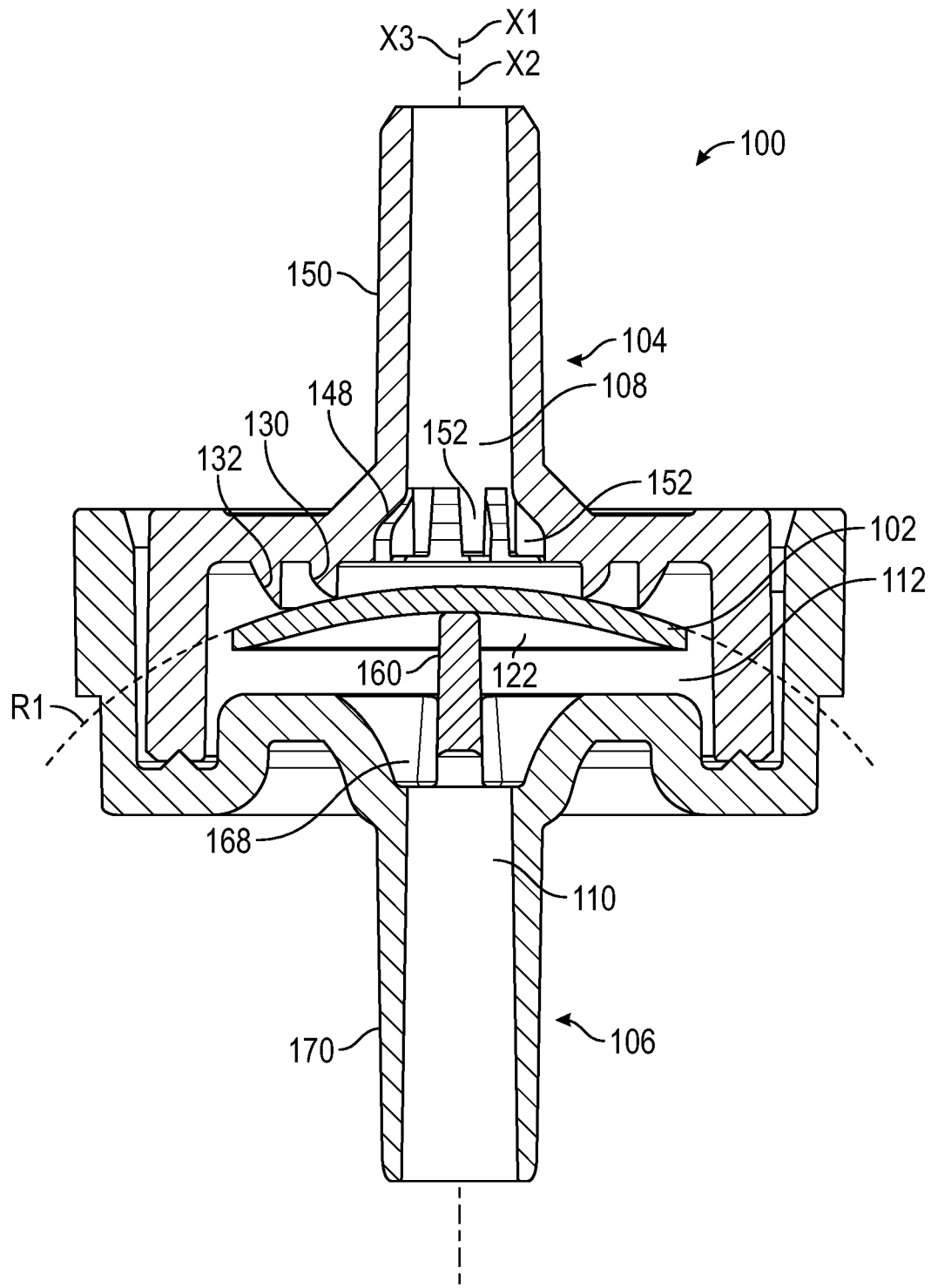
FIG. 3 illustrates a cross-sectional elevation view of the check valve, in accordance with aspects of the present disclosure.

Referring to FIG. 3, a cross-sectional view of the check valve 100 is shown in accordance with some embodiments of the present disclosure. The upper and lower housing 104, 106 are coupled together to form a cavity 112 of the check valve therebetween. A fluid passageway extends through the cavity 112. The valve body 102 separates the fluid passageway into an upstream portion of the fluid passageway 108 and a downstream portion of the fluid passageway 110.

The check valve 100 includes a first sealing surface and a second sealing surface at the upstream portion of the fluid passageway. The first and second sealing surfaces are configured to be engaged against by the valve body 102 depending on a pressure or movement of a fluid in the check valve 100. The first sealing surface can be defined by a first sealing ridge 130, and the second sealing surface can be defined by a second sealing ridge 132. The check valve 100 can also include a valve support structure at the downstream portion of the fluid passageway 110. The valve support structure can be defined by a valve support 160 at the downstream portion of the fluid passageway.

The valve body 102 is seated between a first sealing ridge 130 and a second sealing ridge 132 at the upstream portion of the fluid passageway, and the valve support 160 at the downstream portion of the fluid passageway.

It should be understood that although the present disclosure includes reference to the upper and lower housing 104, 106, any of the first and second sealing ridges 130, 132, and the valve support 160 can be formed as a portion of another structure adjacent to the valve body 102. For example, the first and second sealing ridges 130, 132 can be formed as a component positioned within a fluid pathway and adjacent to a valve body 102. The first and second sealing ridges 130, 132, and the valve support 160, can be associated with a fluid pathway of a device such as a pump, or within a heart ventricle. In another example, the first and second sealing ridges 130, 132, and the valve support 160, can be formed as a portion of a surface in a device, such as a pump.

Referring to FIGS. 2 and 3, the valve body 102 can be shaped as a disk with a top surface 120 and a bottom surface 122. The valve body 102 can have a curved or bowl shape, where at least a portion of the top surface 120 is convex and at least a portion of the bottom surface 122 is concave. In some embodiments, at least a portion of the valve body 102 is flat.

The valve body 102 is positioned in the cavity 112 with the bottom surface 122 of the valve body engaged against the valve support 160 and the top surface 120 of the valve body engaged against the first sealing surface.

The valve body can be formed with the convex top surface 120 having a radius R1. The radius R1 is selected such that, when the valve body 102 is positioned in the cavity 112, the first portion 124 of the valve body engaged against the first sealing ridge 130, and the second portion 126 of the valve body spaced apart from the second sealing ridge 132.

In some embodiments of the present disclosure, the valve body 102 is positioned in the cavity 112 with the first portion 124 of the valve body spaced apart from the first sealing ridge 130, and the second portion 126 of the valve body engaged against the second sealing ridge 132.

The valve body 102 can comprise a material that is flexible, relative to the upper and lower housing 104, 106. In some embodiments of the present disclosure, the valve body 102 include a first segment and a second segment, wherein the second segment is more flexible, relative to the first segment. For example, the first segment of the valve body 102 can comprise the portion of the valve that is configured to engage against the valve support 160 (e.g., the third portion 128 of the valve body), and the second segment of the valve body 102 can comprise the portion of the valve that is configured to engage against the first and second sealing ridges 130, 132 (e.g., the first and second portions 124, 126 of the valve body). In embodiments of the present disclosure, the first segment of the valve can comprise a bottom surface of the valve body or ribs that extend radially outward from an axial center of the valve body. In yet another embodiment of the present disclosure, the first segment of the valve can comprise a ring that extends around a circumference of the valve body 102.

The valve body 102 can be configured to be in a partially flexed or biased orientation when positioned in the cavity 112 defined by the upper and lower housing 104, 106. For example, the valve body 102 can be biased when seated between the first sealing ridge 130 and the valve support 160.

The upper and lower housing 104, 106 can couple together to define the upstream and downstream portions of the fluid passageway 108, 110, which can direct a fluid through the check valve 100. Further, the upper and lower housing 104, 106 can resist unintended movement of the valve body 102 relative to the portion of the upper and lower housing 104, 106. In some embodiments of the present disclosure, the check valve 100 can include a unitary or monolithic housing, or a housing having one or more portions coupled or formed together.

FIGS. 3-6 illustrate a check valve 100 having an upper housing 104 and a lower housing 106 coupled together to define the cavity 112, as well as the upstream and downstream portions of the fluid passageway 108, 110.

Figure 4:
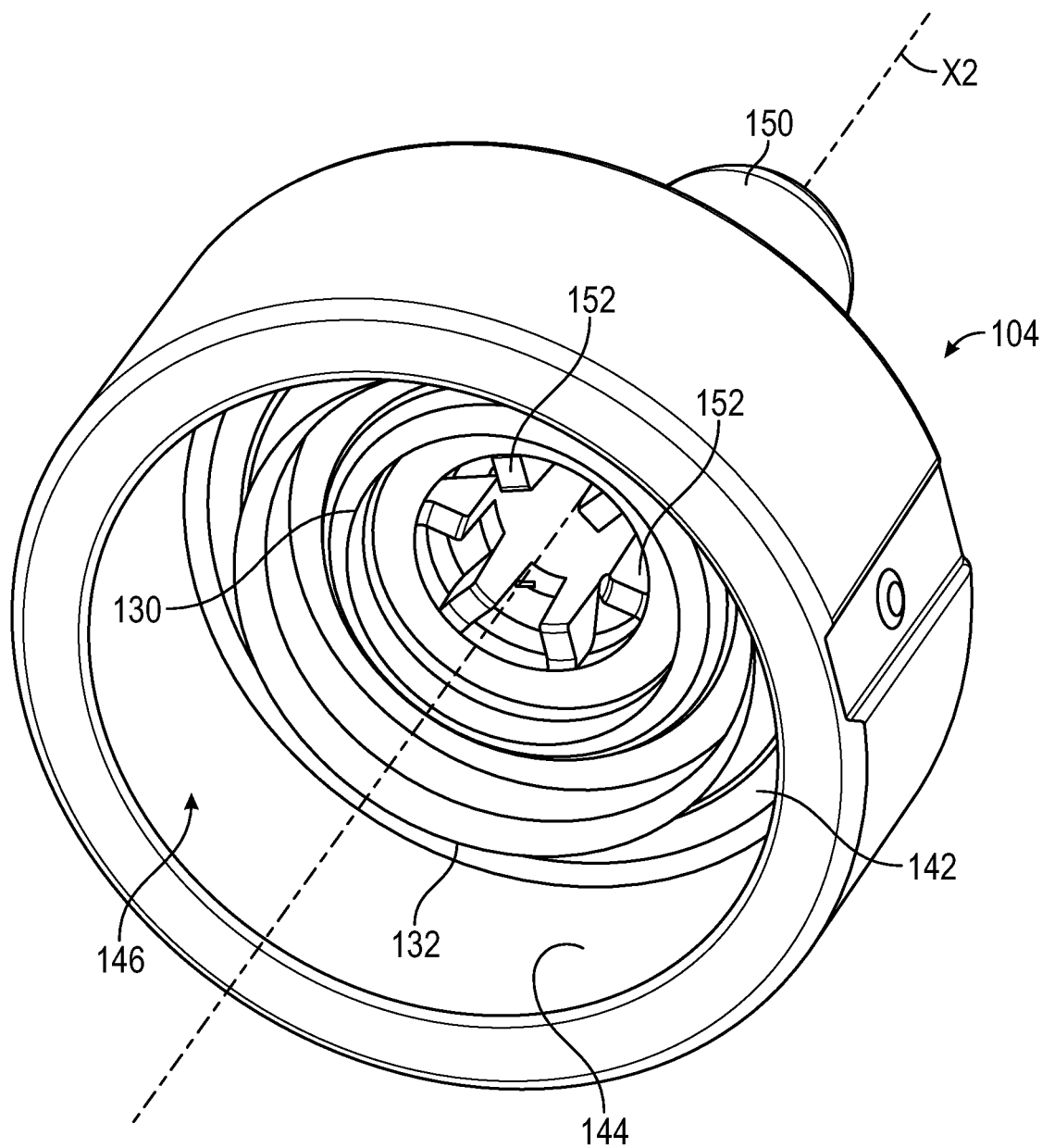
FIG. 4 illustrates a perspective view of a upper housing of the check valve, in accordance with aspects of the present disclosure.

The upper housing 104, shown in isolation in FIG. 4, includes a body defining a central axis X2, a radial wall 142, and a lateral wall 144. The radial wall 142 extends in a direction that is transverse relative to the axis X2, and the lateral wall 144 extends from the radial wall 144 in a direction that is approximately parallel with the axis X2.

At least a portion of the inner surfaces of the radial wall 142 and the lateral wall 144 define a cavity 146 of the upper housing. When the upper and lower housing 104, 106 are coupled together, the cavity 146 of the upper housing and a portion of the lower housing 106 define the cavity 112 of the check valve.

The upper housing 104 can include a first port 148 that defines an opening extending through the radial wall 142. The first port 148 forms a fluid inlet into the cavity 146 of the upper housing. In some embodiments, a portion of the inner surface of the radial wall 142 and the first port 148 are concave, or extend away from the cavity 146 of the upper housing.

The upper housing 104 can also include a sleeve 150 that is configured to couple with a portion of a tubing. The sleeve 150 extends from the radial wall 142 in a direction away from the cavity 146 of the upper housing and approximately parallel to the axis X2. An inner surface of the sleeve 150 and the first port 148 define a passage extending between an outer surface of the upper housing 104 and the cavity 146 of the upper housing. The upstream portion of the fluid passageway 108 can extend through the sleeve 150, the first port 148, and the cavity 146 of the upper housing.

In accordance with some embodiments, the upper housing may include at least one axially extending wall 152 that protrudes radially inward from the inner surface of the radial wall 142 and/or the sleeve 150. The at least one wall 152 may be configured as a protruding surface which is disposed directly above or upstream of the valve body 102. The at least one wall 152 may protrude radially inward from the concave portion of the inner surface defined by the radial wall 142, the sleeve 150, and the first port 148. The at least one wall 152 resists movement of the valve body 102 in a direction from the cavity 146 of the upper housing toward the first port 148 when excessive back pressures are experienced in the check valve 100. For example, an excessive back pressure exerted on the valve body 102 may cause the valve body to deflect or bend to such an extent that the valve body 102 becomes dislodged from the seated position between the valve support 160 and the first sealing ridge 130. If the valve body 102 becomes dislodged from the seated position, the valve body 102 can move through the first port 148, thereby obstructing the upstream portion of the fluid passageway 108 and preventing the check valve 100 from functioning as intended.

Accordingly, when excessive back pressures are experienced in the check valve 100, the valve body 102 can move toward the first port 148 until the valve body 102 engages against the at least one wall 152. When the valve body 102 engages against the at least one wall 152, further movement of the valve body 102 toward the first port 148 is resisted.

The upper housing 104 can also define the first and second sealing surfaces for the valve body 102. The first and second sealing surfaces are formed by a first sealing ridge 130 and a second sealing ridge 132, respectively. Each of the first and second sealing ridges 130, 132 are configured to be engaged against by the valve body 102.

The first and second sealing ridges 130, 132 extend from the radial wall 142 into the cavity 146 of the upper housing. The first and second sealing ridges 130, 132 have a perimeter that extends around the upstream portion of the fluid passageway 108. The perimeter of the first and second sealing ridges 130, 132 are shaped as a circle that extends around the first port 148. However, the perimeter of any of the first and second sealing ridges 130, 132 can have a regular shape, such as an oval, a square, a rectangle, or a triangle, and/or an irregular shape, such as an irregular polygon. In some embodiments of the present disclosure, the first sealing ridge 130 has a different perimeter shape than the second sealing ridge 132.

The perimeter of the first sealing ridge 130 extends around the axis X2 of the upper housing 104, and the second sealing ridge 132 extends around the first sealing ridge 130. The perimeter of the second sealing ridge 132 is positioned radially outward from the first sealing ridge 130, relative to the axis X2. Thus, the first sealing ridge 130 is positioned between the upstream portion of the fluid passageway 108 and the second sealing ridge 132.

Figure 5:
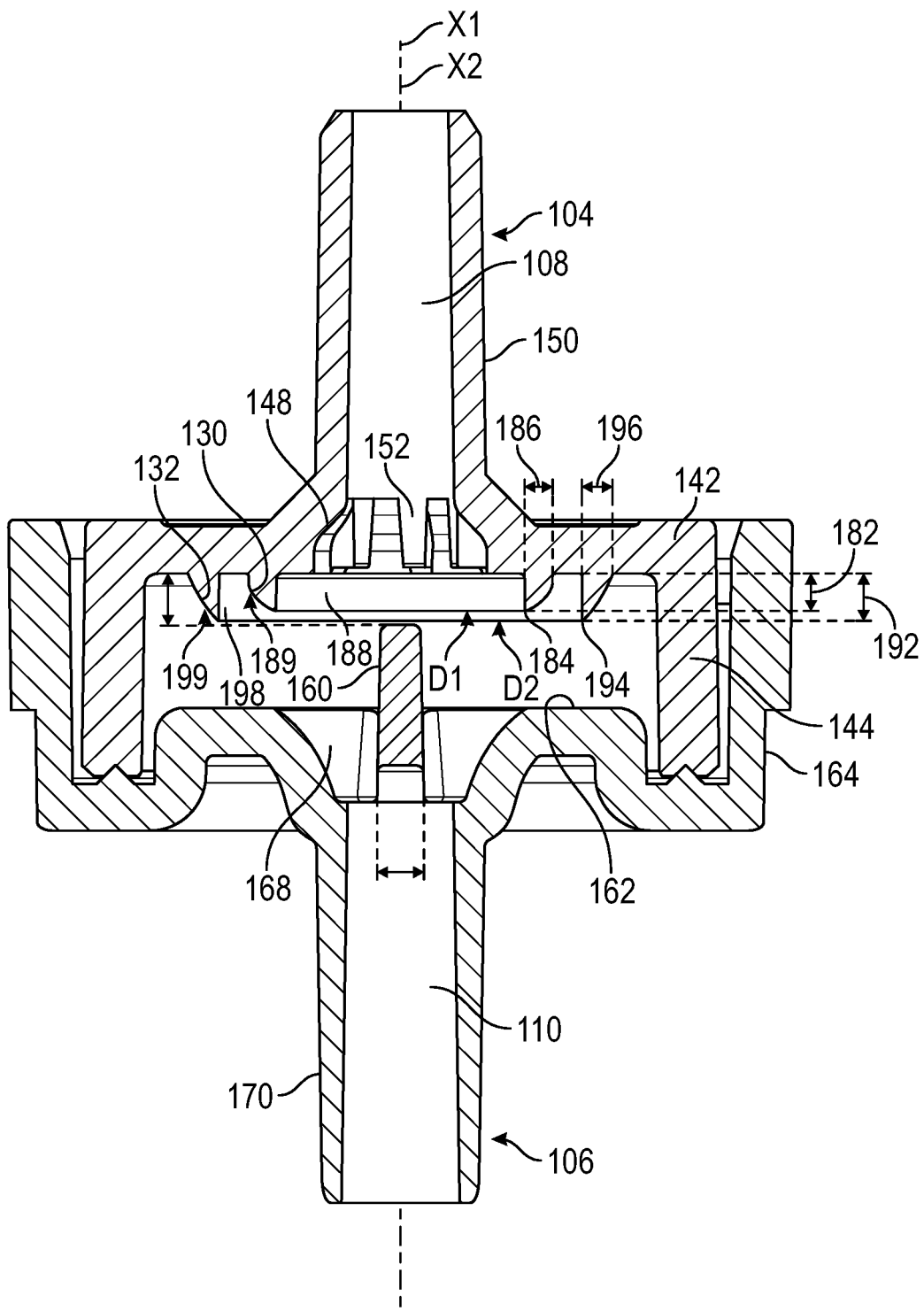
FIG. 5 illustrates a cross-sectional elevation view of the check valve without a valve body, in accordance with aspects of the present disclosure.

Referring to FIG. 5, a cross-sectional view of the check valve 100, taken along the line 5-5, is illustrated. The check valve 100 is shown without the valve body 102 for ease of viewing the first and second sealing ridges 130, 132. The first sealing ridge 130 has a length 182 that extends from the inner surface of the radial wall 142 to an apex 184 of the first sealing ridge. The first sealing ridge 130 also has a width 186 that tapers away from the inner surface of the radial wall 142 toward the apex 184. In some embodiments of the present disclosure, the width 186 of the first sealing ridge 130 tapers along a first segment at a first angle from the inner surface of the radial wall 142 toward the apex 184, and tapers at a second angle from the first segment to the apex 184 at a second angle, where the second angle is greater than the first angle.

In some embodiment of the present disclosure, the first sealing ridge 130 has an inner surface 188 that extends from the inner surface of the radial wall 142 in a direction that is parallel to the axis X2, and an outer surface 189 that extends from the inner surface of the radial wall 142 in a direction that is transverse relative to the inner surface 188. The inner and outer surfaces 188, 189 of the first sealing ridge 130 intersect at the apex 184 of the first sealing ridge.

The second sealing ridge 132 has a length 192 that extends from the inner surface of the radial wall 142 to an apex 194 of the first sealing ridge. The second sealing ridge 132 also has a width 196 that tapers away from the inner surface of the radial wall 142 toward the apex 194. In some embodiments of the present disclosure, the width 196 of the second sealing ridge 132 tapers along a first segment at a first angle from the inner surface of the radial wall 142 toward the apex 196, and tapers at a second angle from the first segment to the apex 194 at a second angle, where the second angle is greater than the first angle.

In some embodiment of the present disclosure, the second sealing ridge 132 has an inner surface 198 that extends from the inner surface of the radial wall 142 in a direction that is parallel to the axis X2, and an outer surface 199 that extends from the inner surface of the radial wall 142 in a direction that is transverse relative to the inner surface 198. The inner and outer surfaces 198, 199 of the second sealing ridge 132 intersect at the apex 194 of the second sealing ridge.

The apex 184 of the first sealing ridge 130 defines a first diameter D1, and the apex 194 of the second sealing ridge 132 defines a second diameter D2. The second diameter D2 is larger than first diameter D1 such that the second sealing ridge 132 is positioned radially outward from the first sealing ridge 130. The second diameter D2 can be larger than first diameter D1 such that the inner surface 198 of the second sealing ridge is spaced apart from the outer surface 189 of the first sealing ridge.

A channel may be formed between first and second sealing ridges 130, 132. In some aspects of the present disclosure, a portion of the inner surface of the radial wall 142 extends between the first and second sealing ridges 130, 132 to form the channel. In some embodiments of the present disclosure, the first and second sealing ridges 130, 132 can be formed by one or more channel that extends into the inner surface of the radial wall 142.

Figure 6:
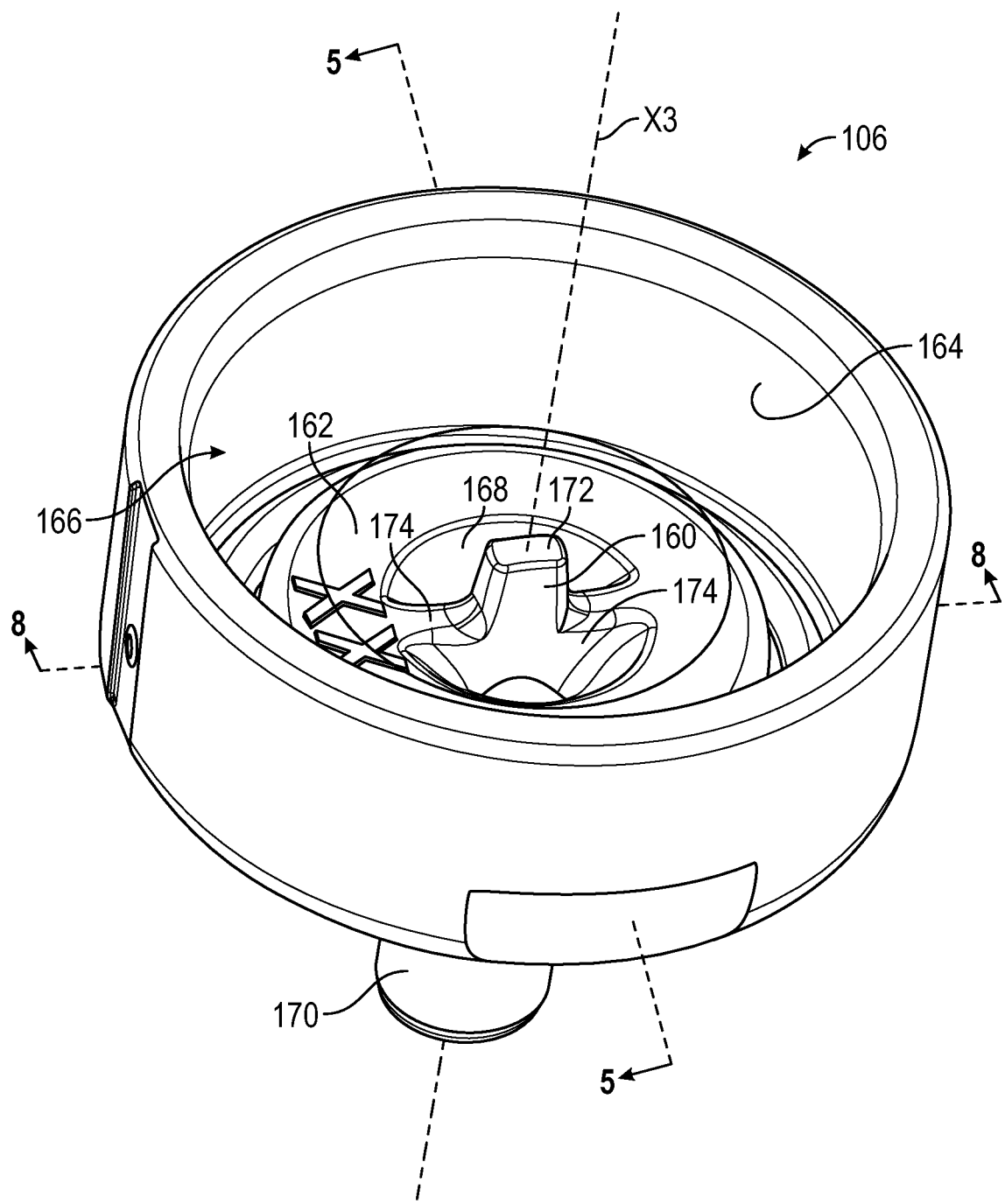
FIG. 6 illustrates a perspective view of an lower housing of the check valve, in accordance with aspects of the present disclosure.

The lower housing 106, shown in isolation in FIG. 6, includes a body defining a central axis X3, a radial wall 162, and a lateral wall 164. The radial wall 162 extends in a direction that is transverse relative to the axis X3, and the lateral wall 164 extends from the radial wall 164 in a direction that is approximately parallel with the axis X3.

At least a portion of the inner surfaces of the radial wall 162 and the lateral wall 164 define a cavity 166 of the lower housing. When the upper and lower housing 104, 106 are coupled together, the cavity 166 of the lower housing and a portion of the upper housing 104 define the cavity 112 of the check valve.

The lower housing 106 can include a second port 168 that defines an opening extending through the radial wall 162. The second port 168 forms a fluid outlet from the cavity 166 of the lower housing. In some embodiments, a portion of the inner surface of the radial wall 162 and the second port 168 are concave, or extend away from the cavity 166 of the lower housing.

The lower housing 106 can also include a sleeve 170 that is configured to couple with a portion of a tubing. The sleeve 170 extends from the radial wall 162 in a direction away from the away from the cavity 166 of the lower housing and approximately parallel to the axis X3. An inner surface of the sleeve 170 and the second port 168 define a passage extending between an outer surface of the lower housing 106 and the cavity 166 of the lower housing. The downstream portion of the fluid passageway 110 extends through the sleeve 170, the second port 168, and the cavity 166 of the lower housing.

In accordance with some embodiments, the check valve 100 may optionally include a valve support 160 configured to engage against a portion of the valve body 102 to retain the valve body in the check valve 100. The valve support 160 can also resist movement of the valve body 102 toward the downstream portion of the fluid passageway 110 or out of the cavity 112.

In some embodiments of the present disclosure, the valve support 160 is a portion of the lower housing 106. The valve support 160 can engage against and resist movement of the valve body 102 in a direction from the cavity 166 of the lower housing toward the second port 168 when fluid flow moves from the upstream portion of the fluid passageway 108 to the downstream portion of the fluid passageway 110.

The valve support 160 extends into the cavity 166 of the lower housing, and is positioned below or downstream of the valve body 102. The valve support 160 may include a base portion and a distal end portion. The base portion of the valve support 160 is coupled with the lower housing 106 and the distal end portion defines a valve support surface 172. The valve support surface 172 is configured to engage against the bottom surface 122 of the valve body 102, along the third portion 128 of the valve body.

In accordance with some embodiments, the lower housing may include at least one arm 174 that protrudes radially inward from the inner surface of the radial wall 162. The at least one arm 172 may be configured as a protrusion that extends between the lower housing 106 and the valve support 160. In some embodiments of the present disclosure, the check valve 100 includes two arms 174, which extend in radially opposing directions, from the concave portion of the inner surface defined by the radial wall 162 to the valve support 160. The two arms 174 position the valve support 160 in the downstream portion of the fluid passageway 110. In some embodiments, the valve support extends along the axis X3.

The valve support 160 may have a width 176 that tapers away from the inner surface of the radial wall 162 toward the valve support surface 172. When the upper housing 104 and lower housing 106 are coupled together, a distance 178 between the valve support surface 172 and the inner surface of the radial wall 142 is greater than the length 182 of the first sealing ridge and the length 192 of the second sealing ridge. In some embodiments of the present disclosure, the distance 178 between the valve support surface 172 and the inner surface of the radial wall 142 is approximately equal to the length 192 of the second sealing ridge, such that a plane defined by the valve support surface 172 intersects a plane defined by the apex 194 of the second sealing ridge.

The check valve 100 is assembled as shown in FIGS. 2 and 3. To assemble the check valve 100, the upper housing 104 and lower housing 106 are coupled together with the valve body 102 therebetween. Before coupling the upper and lower housing 104, 106, the valve body 102 is placed against either of the first or second sealing ridges 130, 132 of the upper housing 104, or the valve support 160 of the lower housing 106. Next, the upper and lower housing 104, 106 are moved toward each other so that the cavity 146 of the upper housing and the cavity 166 of the lower housing define the cavity 112 of the check valve.

In some aspects of the present disclosure, when the check valve 100 is assembled, the axis X2 of the upper housing 104 and the axis X3 of the lower housing 106 are aligned with the axis X1 through the check valve 100.

When the upper and lower housing 104, 106 are coupled together, the bottom surface 122 of the valve body is engaged against the valve support 160, and the top surface 120 of the valve body is engaged against the first sealing ridge 130. More specifically, the valve body can be positioned within the cavity 112 with the first portion 124 of the valve body engaged against the first sealing ridge 130, and the third portion 128 of the valve body engaged against the valve support surface 174.

The valve body 102 can be formed as a disk with the top surface having a radius R1 such that, when the upper and lower housing 104, 106 are coupled together, the first portion 124 of the valve body engages against the apex 184 of the first sealing ridge, and the second portion 126 of the valve body is spaced apart from the apex 194 of the second sealing ridge.

In some embodiments of the present disclosure, the valve body 102, or a portion thereof, can have an approximately flat disc shape. As such, when the upper and lower housing 104, 106 are coupled together, the valve body 102 is biased or bent between the apex 184 of the first sealing ridge and the valve support surface 174.

The valve body 102, or a portion of thereof, is flexible or moveable so that the first portion 124 of the valve body is moveable toward or away from the first sealing ridge 130, and the second portion 126 of the valve body is moveable toward or away from the second sealing ridge 132.

FIG. 3 illustrates the check valve 100 with the valve body 102 in a first closed position. The valve body 102 may be in the first closed position when no fluid is moving through the check valve 100 or when a difference between the fluid pressures of the upstream and downstream portions of the fluid passageway 108, 110, is less than or equal to the cracking pressure of the check valve 100. For example, the valve body 102 may be in the first closed position when a fluid pressure at the upstream portion of the fluid passageway 108 is at a first pressure, and the fluid pressure at the downstream portion of the fluid passageway 110 is at a second pressure, and wherein the first and second pressures are approximately equal. In another example, the example, the valve body 102 may be in the first closed position when the second pressure is greater than the first pressure.

In the first closed position, a distance between the first sealing ridge 130 and the first portion 124 of the valve body is less than a distance between the second sealing ridge 132 and the second portion 126 of the valve body.

Figure 7:
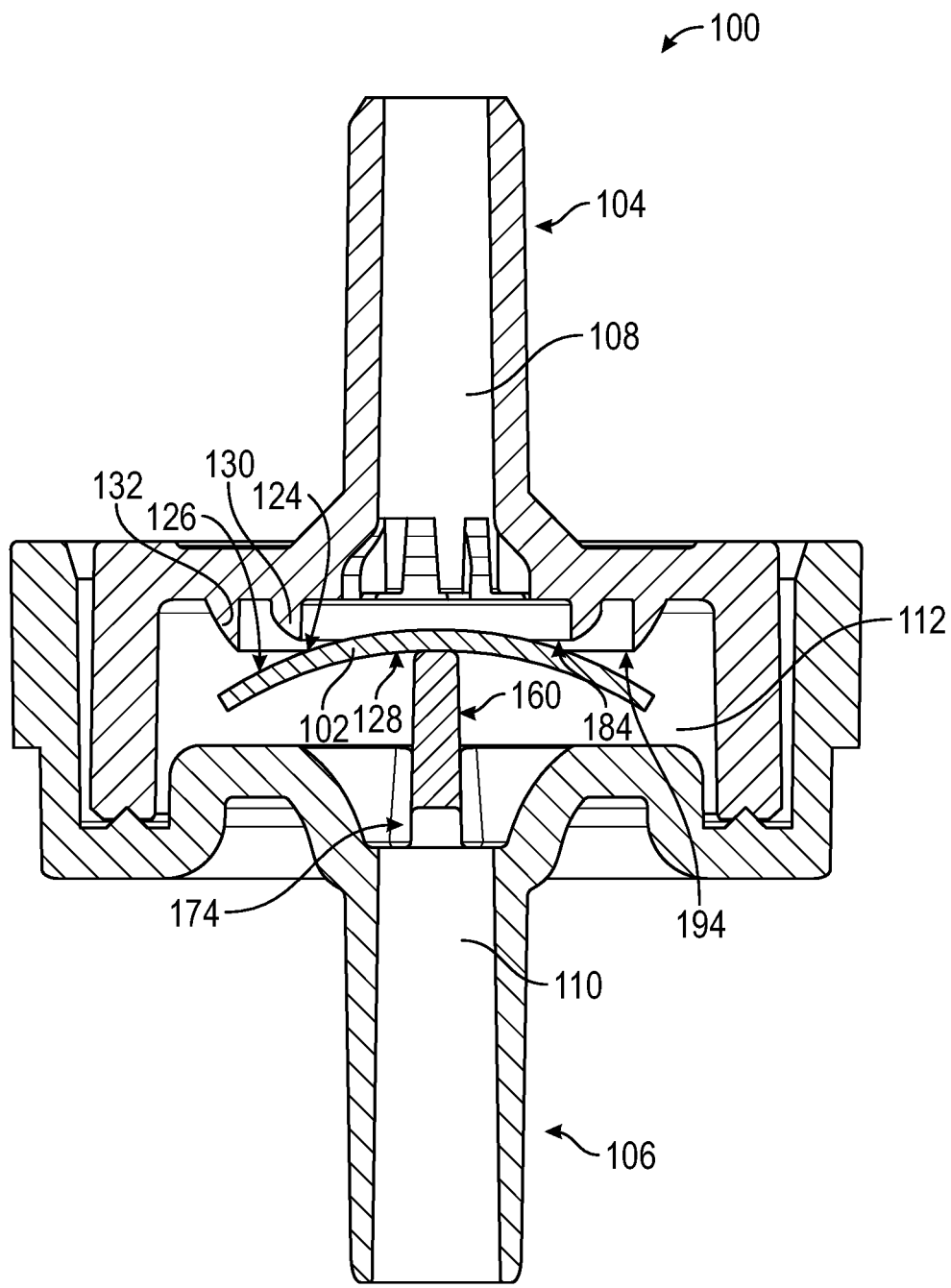
FIG. 7 illustrates a cross-sectional elevation view of the check valve of FIG. 3, in accordance with aspects of the present disclosure.

Referring to FIG. 7, a cross-sectional view of the check valve 100, taken along the line 5-5 is illustrated. The check valve 100 is shown with the valve body 102 in an open position. The valve body 102 may be in the open position when a fluid is moving from upstream portion of the fluid passageway 108 to the downstream portion of the fluid passageway 110, or when the cracking pressure of the check valve 100 is exceeded. For example, the valve body 102 may be in the open position when a fluid pressure at the upstream portion of the fluid passageway 108 is greater than a fluid pressure at the downstream portion of the fluid passageway 110.

In the open position, portions of the valve body 102 including the first portion 124 and the second portion 126 are spaced apart from the first and second ridges 130, 132, respectively. In the open position a fluid can move between the valve body 102 and the first and second ridges 130, 132, from the upstream portion of the fluid passageway 108 to the downstream portion of the fluid passageway 110.

When the valve body 102 moves from the first closed position to the open position, at least a portion of the valve body 102 is flexed or biased so that the distance between the first sealing ridge 130 and the first portion 124 of the valve body is greater than the distance between the first sealing ridge 130 and the first portion 124 of the valve body in the first closed position.

Figure 8:
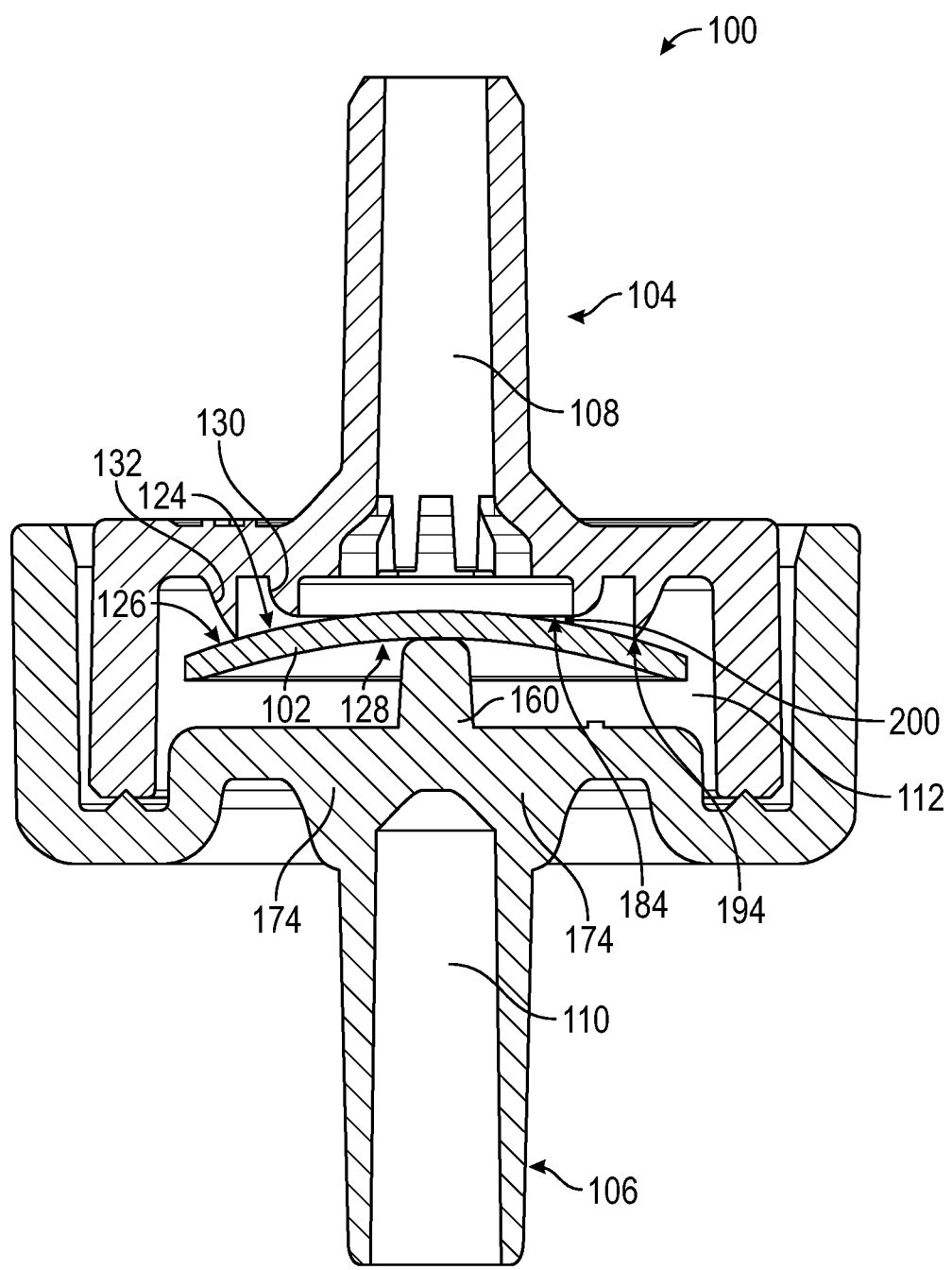
FIG. 8 illustrates a cross-sectional elevation view of the check valve of FIG. 3, in accordance with aspects of the present disclosure.

Referring to FIG. 8, a cross-sectional view of the check valve 100, taken along the line 8-8 is illustrated. The check valve 100 is shown with the valve body 102 in a second closed position. The valve body 102 can move to the second closed position when particulate or debris 200 becomes lodged in the check valve, such that a primary seal is not formed by engagement of the valve body 102 against the first sealing ridge 130. As illustrated, debris 200 is stuck at the interface of the first sealing ridge 130 and the first portion 124 of the valve body. The debris 200 prevents the first portion 124 of the valve body from engaging against the complete perimeter of the apex 184 of the first sealing ridge, thereby permitting a fluid to move or leak from the downstream portion of the fluid passageway 110 to the upstream portion of the fluid passageway 108. When debris 200 or another cause results in failure of the primary seal to be formed as intended, the difference in pressure between the upstream and downstream portions of the fluid passageway 108, 110, cause the second portion 126 of the valve body to move toward and engage against the second sealing ridge 132, thereby forming a secondary or backup seal.

In some aspects of the present disclosure, the valve body 102 moves to the second closed position when the fluid pressure at the downstream portion of the fluid passageway 110 is at a third pressure, which is greater than the first and second pressures.

By providing a first sealing surface and a second sealing surface, the check valve 100 of the present disclosure can form a primary seal with valve body 102 in the first closed position, and can form a backup or secondary seal with the valve body 102 in the second closed position. As such, the check valve 100 of the present disclosure prevents backflow leakage of fluid through the check valve, increases the reliability of the check valve, simplifies manufacturing of the check valve, and increased the efficiency of assembling the check valve.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A check valve comprising: a housing comprising an inner cavity, a first port, and a second port, wherein an upstream fluid passageway extends through the first port to the inner cavity, and a downstream fluid passageway extends through the second port to the inner cavity; a first sealing ridge, extending into the inner cavity, and comprising a perimeter that extends around the first port; a second sealing ridge, extending into the inner cavity, and comprising a perimeter that extends around the upstream fluid passageway such that the first seal ridge is between the first port and the second seal ridge; a valve support comprising a valve support surface; and a valve body positioned within the inner cavity, the valve body comprising a first portion that is moveable relative to the first sealing ridge, a second portion that is moveable relative to the second sealing ridge, and third portion engaged against the valve support surface.

Clause 2. The check valve of Clause 1, wherein the perimeter of the first sealing ridge comprises a first diameter and the perimeter of the second sealing ridge comprises a second diameter, the second diameter being larger than the first diameter.

Clause 3. The check valve of any of Clauses 1 and 2, wherein, a distance between the first sealing ridge and the first portion of the valve body is less than a distance between the second sealing ridge and the second portion of the valve body.

Clause 4. The check valve of any of Clauses 1 to 3, wherein the first sealing ridge comprises a length extending toward the first portion of the valve body, and the second sealing ridge comprises a length extending toward the second portion of the valve body, and wherein the length of the second ridge is greater than the length of the first ridge.

Clause 5. The check valve of Clause 4, wherein any of the first and the second sealing ridges comprise a width that tapers along the length thereof.

Clause 6. The check valve of Clause 5, wherein the width of any of the first and the second sealing ridges tapers away from the housing.

Clause 7. The check valve of any of Clauses 1 to 6, wherein at least a portion of the valve body is flexible such that the first and second portions of the valve body are configured to move toward and away from the first and second sealing ridges, respectively.

Clause 8. The check valve of any of Clauses 1 to 7, wherein the valve body comprises a disk shape having a top surface and a bottom surface, and wherein the top surface comprises the first and second portions of the valve body, and the bottom surface comprises the third portion of the valve body.

Clause 9. The check valve of Clause 8, wherein at least a portion of the top surface comprises a convex surface, and at least a portion of the bottom surface comprises a concave surface.

Clause 10. The check valve of any of Clauses 1 to 9, further comprising a wall that extends into the upstream fluid passageway to resist movement of the valve body out of the inner cavity.

Clause 11. The check valve of Clause 10, wherein the wall extends from the housing into the upstream fluid passageway.

Clause 12. The check valve of any of Clauses 1 to 11, wherein a plane defined an apex of the second sealing ridge is between a plane defined by an apex of the first sealing ridge and a plane defined by the valve support surface.

Clause 13. The check valve of any of Clauses 1 to 12, wherein a plane defined an apex of the second sealing ridge and is spaced apart from a plane defined by an apex of the first sealing ridge.

Clause 14. A check valve comprising: a housing comprising an inner cavity, a first port, and a second port, wherein an upstream fluid passageway extends through the first port to the inner cavity, and a downstream fluid passageway extends through the second port to the inner cavity; a first sealing ridge, extending into the inner cavity, and comprising a perimeter that extends around the first port; a second sealing ridge, extending into the inner cavity, and comprising a perimeter that extends around the upstream fluid passageway such that the first seal ridge is between the first port and the second seal ridge; and a valve body positioned within the inner cavity and comprising a first closed position, wherein a first portion of the valve body is engaged against the first sealing ridge, and a second portion of the valve body is spaced apart from the second sealing ridge, an open position, wherein the first and second portions of the valve body are spaced apart from the first and second sealing ridges, respectively, and a second closed position, wherein at least a portion of the first portion of the valve body is engaged against the first sealing ridge and a second portion of the valve body is engaged against the second sealing ridge.

Clause 15. The check valve of Clause 14, wherein the valve body is in the first closed position when (i) a fluid pressure at the upstream fluid passageway is at a first pressure and the fluid pressure at the downstream fluid passageway is at a second pressure, and wherein the first and second pressures are approximately equal, and (ii) when the second pressure is greater than the first pressure.

Clause 16. The check valve of Clause 15, wherein the valve body is in the second closed position when the fluid pressure at the downstream fluid passageway is at a third pressure, which is greater than the first and second pressures.

Clause 17. The check valve of Clause 15, wherein the valve body is in the open position when the first pressure is greater than the second pressure.

Clause 18. The check valve of any of Clauses 14 to 17, wherein at least a portion of the valve body is flexible such that, in the open position, the first portion of the valve body is biased away from the first sealing ridge.

Clause 19. The check valve of Clause 18, wherein, in the second closed position, the second portion of the valve body is biased toward the second sealing ridge.

Clause 20. A method of controlling flow comprising: providing a check valve defining an inner cavity with a fluid passageway extending therethrough, a first sealing ridge, and a second sealing ridge; and providing a valve body within the inner cavity in a first closed position such that a first portion of the valve body is engaged against the first sealing ridge to resist movement of a fluid between upstream and downstream portions of the fluid passageway, and a second portion of valve body is spaced apart from the second sealing ridge; wherein the valve body is moveable to a second closed position such that at least a portion of the first portion of the valve body is engaged against the first sealing ridge and a second portion of the valve body moves toward and engages the second sealing ridge.

Clause 21. The method of Clause 20, wherein the valve is moveable to an open configuration wherein the first and second portions of the valve are spaced apart from the first and second sealing ridges, respectively, to permit a fluid to move between the upstream and downstream portions of the fluid passageway.

Clause 22. The method of any of Clauses 20 and 21, wherein providing a valve within the inner cavity comprises positioning the valve between a valve support and the first and second sealing ridges.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A check valve comprising:
a housing comprising an inner cavity, a first port, a second port, a first sealing ridge, a second sealing ridge, and a valve support, wherein an upstream fluid passageway extends through the first port to the inner cavity, a downstream fluid passageway extends through the second port to the inner cavity, the first sealing ridge extends into the cavity and comprises a perimeter that extends around the first port, and the second sealing ridge extends into the cavity and comprises a perimeter that extends around the first sealing ridge such that the first seal ridge is between the first port and the second seal ridge; and
a flexible valve body positioned within the inner cavity, the valve body comprising a first segment and a second segment extending between the first segment and an outer perimeter of the flexible valve body, wherein the first segment is engaged against the valve support, the second segment is movable, relative to the first segment, and the second segment comprises a first portion and a second portion, and wherein the first portion is movable relative to the perimeter of the first sealing ridge, and the second portion is moveable relative to the perimeter of the second sealing ridge and the first portion.

2. The check valve of claim 1, wherein the perimeter of the first sealing ridge comprises a first diameter and the perimeter of the second sealing ridge comprises a second diameter, the second diameter being larger than the first diameter.

3. The check valve of claim 1, wherein, a distance between the first sealing ridge and the second segment of the valve body is less than a distance between the second sealing ridge and the second segment of the valve body.

4. The check valve of claim 1, wherein the first sealing ridge comprises a length extending toward the second segment of the valve body, and the second sealing ridge comprises a length extending toward the second segment of the valve body, and wherein the length of the second sealing ridge is greater than the length of the first sealing ridge.

5. The check valve of claim 4, wherein any of the first and the second sealing ridges comprise a width that tapers along the length thereof.

6. The check valve of claim 1, wherein the second segment comprises the outer perimeter of the flexible valve body.

7. The check valve of claim 1, wherein the first portion is moveable in a first direction away from the first sealing ridge and in a second direction toward the first sealing ridge, and the second portion is moveable in the first direction away from the second sealing ridge and in the second direction toward the second sealing ridge.

8. The check valve of claim 1, wherein the valve body comprises a disk shape having a top surface and a bottom surface, and wherein the top surface comprises the second segment of the valve body, and the bottom surface comprises the first segment of the valve body.

9. The check valve of claim 8, wherein at least a portion of the top surface comprises a convex surface, and at least a portion of the bottom surface comprises a concave surface.

10. The check valve of claim 1, further comprising a wall that extends into the upstream fluid passageway to resist movement of the valve body out of the inner cavity.

11. The check valve of claim 1, wherein a plane defined by an apex of the second sealing ridge is between a plane defined by an apex of the first sealing ridge and a plane defined by the valve support.

12. The check valve of claim 1, wherein a plane defined by an apex of the second sealing ridge and is spaced apart from a plane defined by an apex of the first sealing ridge.

13. The check valve of claim 1, wherein the second portion of the second segment forms an entire outer perimeter of the flexible valve body that is movable relative to the housing.

14. A check valve comprising:
a housing comprising an inner cavity, a first port, a second port, a first sealing ridge, a second sealing ridge, and a valve support, wherein an upstream fluid passageway extends through the first port to the inner cavity, a downstream fluid passageway extends through the second port to the inner cavity, the first sealing ridge extends into the cavity and comprises a perimeter that extends around the first port, and the second sealing ridge extends into the cavity and comprises a perimeter that extends around the first sealing ridge such that the first seal ridge is between the first port and the second seal ridge; and
a flexible valve body positioned within the inner cavity and comprising a first segment and a second segment, wherein the second segment is positioned radially outward from the first segment and extends from the first segment to an outer perimeter of the flexible valve body, and, in a first closed position of the valve body, a first portion of the second segment is engaged against the first sealing ridge, in an open position of the valve body, the first portion and a second portion of the second segment are spaced apart from the first and second sealing ridges, and in the first closed position and the open position of the valve body, the second portion is moveable relative to the first portion.

15. The check valve of claim 14, wherein the valve body is in the first closed position when (i) a fluid pressure at the upstream fluid passageway is at a first pressure and the fluid pressure at the downstream fluid passageway is at a second pressure, and wherein the first and second pressures are approximately equal, and (ii) when the second pressure is greater than the first pressure.

16. The check valve of claim 15, wherein the valve body is in the open position when the first pressure is greater than the second pressure.

17. The check valve of claim 15, wherein, in a second closed position, the first and second portions of the second segment are engaged against the first and second sealing ridges.

18. The check valve of claim 17, wherein the valve body is in the second closed position when the fluid pressure at the downstream fluid passageway is at a third pressure, which is greater than the first and second pressures.

19. The check valve of claim 17, wherein, in the second closed position, the second segment of the valve body is biased toward the second sealing ridge.

20. The check valve of claim 14, wherein, in the open position, the second segment of the valve body is biased away from the first sealing ridge.

* * * * *